United States Patent [19]

Booth et al.

[11] Patent Number: 4,879,897

[45] Date of Patent: Nov. 14, 1989

[54] METHOD AND APPARATUS FOR THE DETERMINATION OF VISCOSITY

[75] Inventors: Rodney I. Booth, Newport; David W. Edwards, Fairlight; Colin W. Wrigley, Epping; Robert A. Orth, North Narrabeen, all of Australia

[73] Assignee: Commonwealth Scientific and Industrial Research Organization, Campbell, Australia

[21] Appl. No.: 328,758

[22] Filed: Mar. 23, 1989

Related U.S. Application Data

[63] Continuation of Ser. No. 50,703, filed as PCT AU86/00238 on Aug. 18, 1986, published as WO87/01198 on Feb. 26, 1987, abandoned.

[30] Foreign Application Priority Data

Aug. 19, 1985 [AU] Australia .............................. PH2013
Feb. 13, 1986 [AU] Australia .............................. PH4578

[51] Int. Cl.[4] ........................................... G01N 11/14
[52] U.S. Cl. ...................................................... 73/59
[58] Field of Search ................... 93/59, 60, 54; 137/4, 137/92

[56] References Cited

U.S. PATENT DOCUMENTS

| | | | |
|---|---|---|---|
| 1,924,969 | 8/1933 | Wheeler | 73/60 |
| 2,266,733 | 12/1941 | Bays et al. | 73/59 |
| 2,660,885 | 12/1953 | Evans | 73/59 |
| 2,673,463 | 3/1954 | Kimball et al. | 73/59 |
| 2,679,157 | 5/1954 | Carpenter | 73/59 |
| 2,708,361 | 5/1955 | Boyle et al. | 73/59 |
| 2,759,355 | 8/1956 | Boyle et al. | 73/59 |
| 3,090,223 | 5/1963 | Juffa et al. | 73/59 |
| 3,139,745 | 7/1964 | Sievers et al. | 73/23.1 |
| 3,635,678 | 1/1972 | Seitz et al. | 73/64.1 |
| 4,173,142 | 11/1979 | Heinz | 73/60 |
| 4,283,938 | 8/1981 | Epper et al. | 73/59 |
| 4,299,119 | 11/1981 | Fitzgerald | 73/59 |
| 4,445,365 | 5/1984 | Selby | 73/60 |
| 4,524,611 | 6/1985 | Richon et al. | 73/59 |
| 4,633,708 | 1/1987 | Blommaert | 73/59 |

OTHER PUBLICATIONS

The Amylograph Handbook, Wm. C. Shuey and Keith H. Tipples.

Primary Examiner—Hezron E. Williams
Attorney, Agent, or Firm—Merchant, Gould, Smith, Edell, Welter & Schmidt

[57] ABSTRACT

A method for measuring the viscosity of liquids including homogeneously mixed suspensions at known temperatures is provided. The method concerns rapidly adjusting the temperature of the liquid, stirring the liquid by rotating a stirring arrangement within the liquid at a measured speed, and measuring the power consumed by rotating the stirring arrangement in the liquid. The invention also concerns an arrangement specifically adapted for application of the method. According to both the method and arrangement, a removable vessel for the liquid is provided.

14 Claims, 2 Drawing Sheets

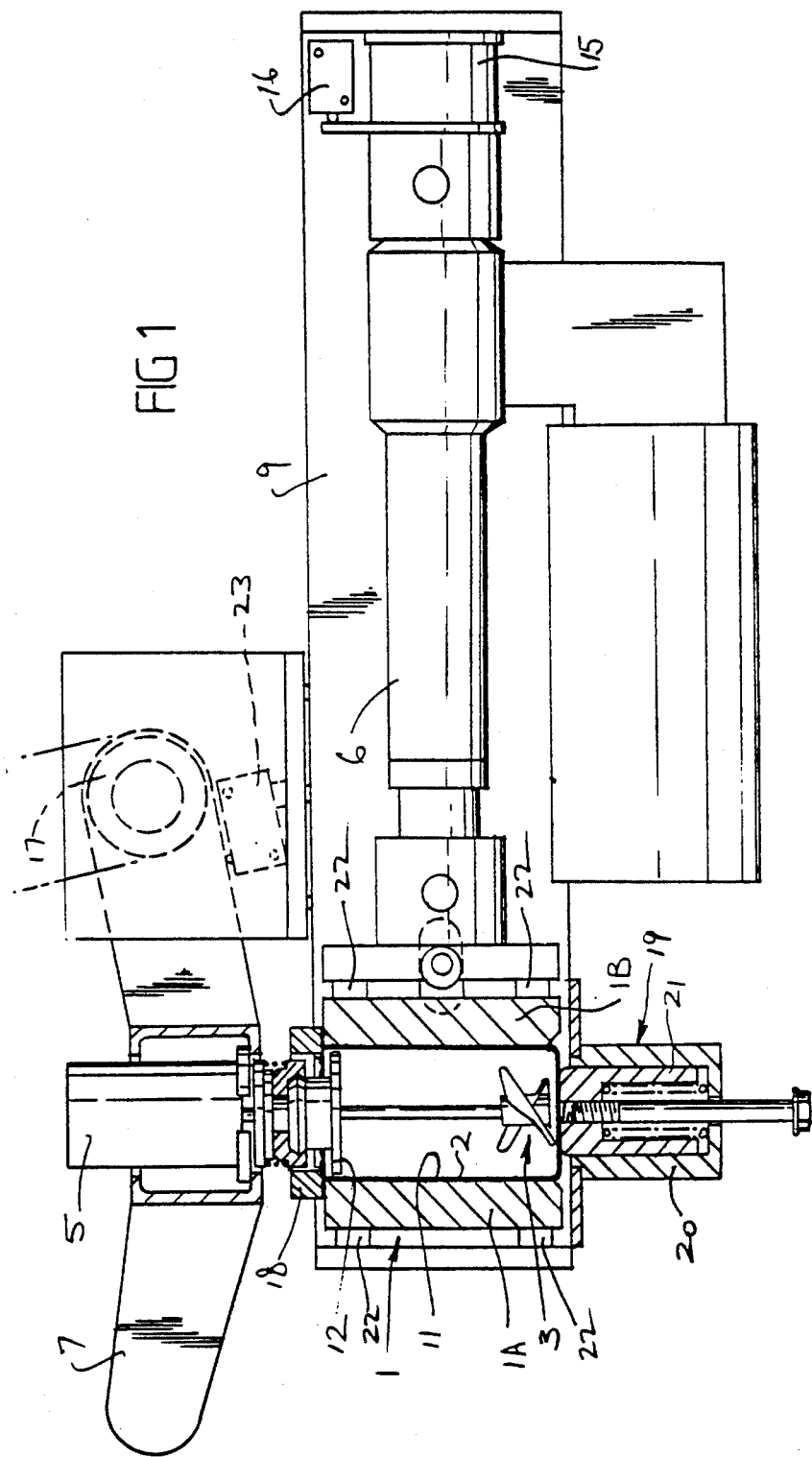

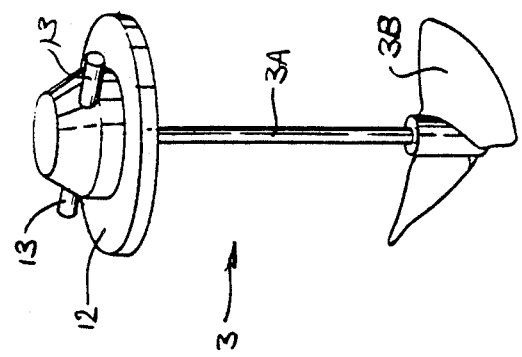
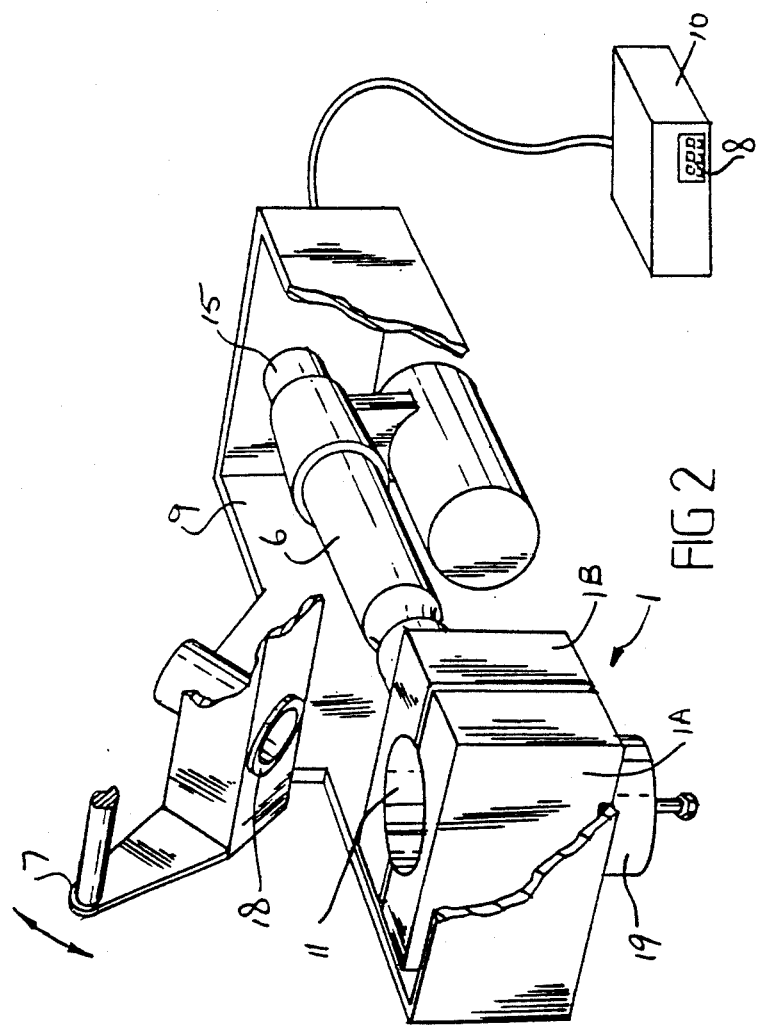

METHOD AND APPARATUS FOR THE DETERMINATION OF VISCOSITY

This is a continuation of application Ser. No. 050,703, filed as PCT AU86/00238 on Aug. 18, 1986, published as WO87/01198 on Feb. 26, 1987, now abandoned.

BACKGROUND OF THE INVENTION

The present invention relates to a method for measuring the viscosity of fluids and suspensions at varying temperatures and to equipment for carrying out the method.

Whilst not limited to such application the present invention is particularly suitable for determining the level of sprouting or germination in cereal grains and derived cereal products. Other applications envisaged include quality control in the food and polymer industries. The term "Fluid" as used throughout this specification is intended to include homogeneously mixed suspensions.

The suitability of cereal grain for making bread and other foodstuffs is affected by the degree of sprouting or germination of the grain before harvest. Natural biological processes connected with the sprouting of cereal crops result in the production of various substances, of which the enzyme amylase has the most notable influence on cereal quality. Amylase reacts with cereal starches causing them to be broken down at a rate which is dependent on amylase level and on temperature. Thus, it is possible to make a reasonably accurate estimate of sprouting activity in a cereal by monitoring the viscosity of an aqueous paste of a sample while it is heated under controlled conditions.

A well-known test which is based on the viscosity change in an aqueous cereal paste during heating is the Falling Number Test, and this involves measuring the time taken for a plunger to fall under gravity through a heated sample.

In the past the Falling Number Test has been performed using bulky equipment and thorough washing of both plunger and vessel has been required following every test. This process has been slow and has required the attendance of skilled personnel.

SUMMARY OF THE INVENTION

The present invention offers a test which is relatively quick, cheap and moreover, readily adapted for substantially automatic operation thereby avoiding a need for skilled personnel or back up laboratory factilities.

According to the present invention there is provided a method for measuring the viscosity of a liquid (as hereinbefore defined) at known temperatures which comprises:

(a) rapidly adjusting the temperature of the said liquid;

(b) stirring said liquid by rotating a stirring means within said liquid at a measured speed; and (c) measuring the power consumed by rotating said stirring means at said speed.

According to another aspect of this invention there is provided a method for determining the degree of sprouting in cerals (which term is to be understood as embracing cereal grain and products) which comprises:

(a) preparing a cereal/water mixture of known proportions;

(b) rapidly adjusting the temperature of said mixture;

(c) stirring said mixture by rotating a stirring means at a measured speed; and (d) measuring the power consumed by rotating said stirring means at said measured speed at a measured period of time or series of time after the commencement of said temperature adjustment.

When used to determine the level of sprouting or germination in cereal grains and derived cereal products the present invention, as with the Falling Number Test, is based largely on the reaction of amylase with starches, but in this case viscosity is indicated by resistance to the rotation of a stirring means in a heated aqueous paste. As the temperature of the mixture increases the starch content of the cereal gelatinizes thus making the mixture more viscous. The activity rate of the amylase rises, attacking the starch, and thus operates to reduce the viscosity of the mixture. These two competing effects create, after a measured time, a paste of a certain viscosity.

It is preferable that the said temperature adjustment and said stirring are commenced substantially simultaneously. As the viscosity of the liquid is related to the temperature of the liquid and the power consumed in rotating the stirring means at a particular speed, viscosity measurements can be commenced almost immediately. It is also preferable that the liquid be retained in a vessel which is brought into contact with a heat transfer means. Most preferably the vessel is clamped within the heat transfer means. Such clamping should be of sufficient strength to slightly deform the walls of the vessel so that they substantially conform to the face of the heat transfer means. In this way it is possible to remove any air gap which may be present between the vessel and the heat transfer means due to the manufacturing tolerances of these components. Such steps enhance the speed at which this method may be carried out.

The heat transfer means may be of any of a number of forms but preferably it is a metallic block. Preferably, the metallic block is axially split into two sections which are adapted to be brought into contact with the vessel. If the liquid being tested is a cereal/water mixture initially it may be necessary to rotate the stirring means relatively rapidly to promote homogenity. The rotation speed of the stirring means may then be reduced, maintained constant by, say, electronic means, and at a known time after the time of temperature adjustment the power being consumed by the motor can be measured.

By way of example the degree of sprouting in a particular cereal may be ascertained by preparing a cereal/water paste of about 25% w/v composition by adding a sample of the cereal (preferably in the form of fine particles) to water at a predetermined temperature in a vessel in clamped contact with a heat transfer means. The degree of sprouting may be derived by relating the power-consumption reading for any particular stirrer rotation speed to tables of readings obtained from testing of control samples, or the equipment may, for example, incorporate circuitry to give a direct readout of sprouting or some other convenient indicator of sample quality.

For increased accuracy it may be desirable to take power consumption measurements at a number of fixed times for comparison with control values. Study of the power consumption curve over a period of time from the commencement of heating may also yield useful information. For example, the whole curve profile may yield a more accurate guide to the Falling Number of the cereal being tested or the properties of the starch or other component of the sample in relation to the suitability for processing.

It will be clear to those skilled in the art that suitable values for parameters such as mixture starting temperatures, heating rates, stirring rates and power consumption measurement times will vary according to the cereal or other substance being tested, and the dimensions of the vessel and associated stirrer. By way of example only, Table I illustrates parameters with which it has been possible to estimate the degree of sprouting to a precision of better than 4% co-efficient of variance using 30 ml samples of a variety of cereals in a heating vessel of 3.8 cm diameter fitted with an irregular-shaped paddle 0.7 deep and 3.2 cm overall width.

TABLE I

| Cereal | Particle Size | Sample Composition % w/v | Heating Block Temp. °C. | Stirring rate for power consumption measurement (rmp) | Time of power consumption measurement (min) |
|---|---|---|---|---|---|
| Wheat | 700 um | 24 | 88 | 300 | 2 |
| Wheat | 700 um | 19 | 95 | 300 | 2 |
| Barley | 700 um | 24 | 88 | 300 | 1.5 |

*Heat was provided by a 600 watt element wound around the heating chamber.
**All samples were initially stirred at 1100 rpm for 15 seconds before reducing the stirrer speed to a constant level at which power consumption was measured.

According to this invention there is also provided an apparatus for measuring the viscosity of a liquid (as hereinbefore defined) which comprises:

(a) a vessel;

(b) a heat transfer means adapted to accommodate said vessel and capable of rapidly adjusting the temperature of its contents;

(c) a stirring means adapted to be positioned within said vessel;

(d) a motor suitable to drive said stirring means;

(e) a speed controller for controlling the speed of the stirring means; and (f) power consumption measurement means for measuring the power consumption of the motor at any given time.

Preferably the motor used to drive the stirrer is an electric motor. The vessel may be made of any suitable material, preferably a heat conductive material and is preferably of a disposal type in order that the vessel does not require cleaning after each test. Most preferably a thin walled (approximately 0.3 mm) aluminium canister is used.

The heat transfer means is preferably a metallic block. Such heating chamber is adapted to accommodate the reaction vessel and preferably is clamped around the reaction vessel in order to achieve a constant heating rate. The heat transfer means may be made out of any heat conductive material and preferably comprises a solid copper or aluminium block. In one embodiment of this invention the heating chamber is further split along an axis (preferably the central axis) and mounted so that one section is fixed and the other portion is free to move. Pressure applying means may further be provided in order to provide a sufficient force to cause the two sections of the heating chamber to be pressed together. Such pressure applying means may be a mechanical actuator attached between the moveable portion of the heating chamber and some other rigidly fixed body such as a retaining framework.

Preferably the pressure applying means is an electrically or mechanically driven mechanism which is automatically activated upon the commencement of the rotation of said stirring means.

Where the heating chamber does comprise two portions a lever system may also be provided for either manual or automatic use to separate the two portions of the heating chamber so as to allow the insertion of the reaction vessel into place. The motor is preferably connected to the stirrer by a coupling so that it may be detached from the stirrer. In a preferred form the stirrer is provided with pins located at either side of the top of the stirrer which are adapted to couple with helical slots located to a fixture at the end of the motor shaft. When the stirrer is coupled to the motor in this way in operation the stirrer top is caused to automatically rise slightly and thus clear the rim of the vessel and thereby remove any unwanted frictional factors.

As stated it is important that the equipment provide means for driving the stirrer at a known speed. Accurate speed control of the motor can be achieved through the use of electronics. Depending on the agitation of the mixture in the vessel by the stirrer, more or less heat will be conducted into the mixture. Preferably, the motor speed should be controlled to better than $+1\%$.

Similarly the temperature of the heating chamber should be accurately determinable and controllable for tests of different grains or liquids.

Another feature which is provided in a preferred embodiment of this invention is the facility to accurately time the initiation of the heating effect. As the heat transfer means transmits negligible heat to the vessel prior to the clamping action it is the clamping action which is preferably used to trigger the test cycle.

In this way the instrument operation is not affected in any way by operator inexperience or facility. Where a lever system is provided a microswitch can be used to this effect attached to the lever system and monitored by a microprocessor—the operation of the microswitch initiating a test cycle.

The equipment of this invention may therefore also be provided with instrument electronics comprising some or all of the following sub units:

(a) Speed controller—such controller controls the motor speed—preferably for testing sprouting damage the stir speed is 800 r.p.m. whereas the measure speed is preferably 200 r.p.m.

(b) Temperature controller—such controller controls the temperature of said chamber. Preferably this is variable from between 25° C. and 100° C. for testing of starch properties and for testing wheat for sprouting damage is most preferably set at approximately 92° C.

(c) Analog to Digital convertor—Where an electric motor is used the motor current is usually in the range of 0 to 0.2 Amperes, depending on the viscosity of the test mixture. This current may be converted to a digital number by an analog to digital convertor and further converted by a look up table is generated empirically to yield a display result proportional to motor power and adjusted to correlate with other known and accepted indexes of sprout damage. The look up table closely models a parabolic relationship of the form:

$$x = 500(10i^2 + 3i)$$

where i—motor current and x=displayed result.

(d) Display—The result may be displayed as a three digit number in the range 0–500 on a Light Emitting Diode digital display.

In the operation of the preferred method a weighed, ground wheatmeal or starch sample is placed in the vessel with a measured quantity of water. The motor is positioned over the vessel and is connected to the stirrer. The heat transfer means is brought into contact with the vessel simultaneously with the initiation of the rotation of the stirring means and heat is conducted into the sample through the walls of the reaction vessel. This causes the starch to gelatinize. The motor is first set to operate at a fast, or mix, speed to suspend the particles of the mixture and is then slowed to a measuring speed at which time the power being consumed by the motor is measureds. A preferred embodiment of the equipment provided by the present invention is hereafter described with reference to the accompanying drawings.

BRIEF DESCRIPTION OF THE DRAWINGS

FIG. 1 is side elevation of the mechanical assembly of an apparatus made in accordance with the invention, partially sectioned.

FIG. 2 is a perspective view of an apparatus made in accordance with the invention.

FIG. 3 is a perspective view of a stirring paddle used in the apparatus of the invention.

DETAILED DESCRIPTION OF THE INVENTION

A heating chamber 1 is formed from a solid metal block fitted with suitable electrical heating elements (not shown) and is dimensioned approximately 70×65×65 mm.

This heating chamber is axially split into two portions. The first half 1A is fixed. The second half 1B is moveable. The fixed portion 1A and moveable portion 1B are shaped such that when they are pressed together there is provided a cylindrical recess 11. Attached to the moveable portion 1(B) is a mechanical actuator 6. Mounting of the blocks is achieved by insulating supports 22. The actuator 6 coacts against the end wall of the framework 9 at its remote end via a rubber spring 15. Force applied by the mechanical actuator 6 is controlled by compression of the rubber spring 15 interrupting (via a microswitch 16) the current to the actuator 6. Preferably mechanical actuator 6 applies a force of approximately 1500 Newtons on the heating chamber 1.

The cylindrical recess 11 is of a diamter which when the two halves of the heating chamber are brought together the reaction vessel 2 is forced to conform to the walls of the recess 11, and contact is obtained substantially over the whole area of the sides of the reaction vessel 1. The reaction vessel 2 is a thin walled (0.3 mm) aluminium canister annealled to improve conformability.

A rotatable stirrer 3 is provided which comprises a stem 3A and paddle 3B. The stirrer 3 is adapted to be received into the reaction vessel 1. At the top of the stirrer 3 there is provided a plate 12 and coupling pins 13.

An electric motor 5 is positioned above the reaction vessel 2 and is connected by a helical coupling (not shown). A lever 7 is positioned to pivot on bearings 17 which also carries motor 5. When lever 7 is brought forward and down motor 5 is accurately positioned over the central axis of the reaction vessel 2.

Also connected to lever 7 is an annular shaped buffer ring 18 fabricated from non heat conductive material such as nylon. The buffer ring 18 pushes the reaction vessel down into the cylindrical recess 11 against the pressure of the ejection assembly 19. The ejection assembly is comprised of body 20 and spring loaded plunger 21.

The heating chamber 1 and mechanical actuator 6 are mounted within framework 9. Electric motor 5 is electrically connected to case 10 which contains electronic components which cannot be seen in the figures. The electronic components contained in case 10 include a microprocessor which controls the following sub units:

(a) a speed controller which controls the speed of the electric motor;

(b) a temperature controller which enables control of the heating chamber and (c) an analog to digital convertor which converts the current utilized by the motor to a digital number and further converted by a look up table held in memory to give a test result.

A digital display 8 is provided at the front of case 10 and is of the light emitting diode type.

In operation lever 7 is lifted up and back to expose recess 11 in the block 1. Switch 23 signals the electronics to relax the actuator 6 thus parting the halves of the block 1A and 1B. Reaction vessel 2 containing a sample for analysis and stirrer 3 is placed into recess 11 until the base of reaction vessel 2 is in contact with the ejecter plunger 21 (being in its raised position). Handle 7 is then pivoted forward bringing buffer ring 18 in contact with the rim of the reaction vessel 2. Hand pressure on lever 7 forces the vessel 2 down against the plunger 21 which retracts into the plunger body 20, until the buffer ring 18 contacts the upper surface of the blocks 1A and 1B. Switch 23 signals the electronics to close the actuator, moving block 1B against block 1A and hence slightly deforming the reaction vessel 2 in the recess 11.

In operation lever 7 is moved back to open heating chamber 1. Reaction vessel 2 containing a sample such as a weighed ground wheatmeal or starch sample is partially filled with a measured quantity of water and is then placed into the recess between the fixed portion 1(A) of heating chamber 1 and the moveable portion 1(B) of heating chamber 1. The lever system 7 is released and the mechanical actuator 6 exert a pressure on moveable portion 1(B) of heating chamber 1 causing the separated portions 1(A) and 1(B) to clamp the reaction vessel 2 firmly. As the reaction vessel 2 has relatively thin walls the clamping force is sufficient to deform the walls of the reaction vessel 2 to the shape of cylindrical recess 11. This removes any slight air gap which may be present between reaction vessel 2 and the walls of cylindrical recess 11 and promotes more efficient and rapid heating of reaction vessel 2 and hence its contents.

As the actuator 6 continues to run, the opposing faces of blocks 1A and 1B will met and then rubber spring 15 compresses. When the required compression and hence clamping force is achieved switch 16 signals the electronics to halt the actuator 6 which is self locking.

At the same time switch 23 signals the electronics to cause the motor 5 to rotate. The helical slots in the coupling at the end of motor 5 engage with pins 13 and the stirrer 3 is lifted clear of the base of the vessel 2 to remove friction between the two.

In another embodiment, a frusto conical canister is used as sample container, being forced from above into close contact with a heating block of matching shape.

Heating of the heating chamber 1 is provided by a resistance within the block and a temperature sensor may also be mounted within the heating chamber 1, the whole being thermally insulated. Heat is conducted into the sample through the walls of the reaction vessel and if the sample contains a cereal gelatinises the starch. The motor is first run at a speed of approximately 800 r.p.m. to mix the solution and suspend the particles of the mixture and then run at a slower speed of approximately 200 r.p.m. for measurement of the viscosity.

The viscosity of the sample is converted by the microprocessor (as previously described) and presented to the user as a digital result or analog signal for further display either on the digital display 8 or a chart record (not shown).

At completion of the test cycle the actuator 6 is opened releasing reaction vessel 2. Then at any convenient time for the operator the lever 7 is lifted and the reaction vessel 2 is ejected by plunger 21 to a point where the vessel can be removed completely by the operator and discarded.

As preferably stated the equipment described has application in any situation where viscosity of fluids must be determined. In particular, where viscosity at higher or lower temperatures is required, the precision obtained by the heating chamber described is especially useful. It is obviously possible and within the ambit of the present invention to fit an electronic cooler to the heating chamber to provide low temperature or heat/-cooled cycle viscosities.

Finally it is to be understood that various alterations, modifications and/or additions may be introduced into the constructions and arrangements of parts previously described without departing from the spirit or ambit of the invention.

We claim:

1. A method for measuring the viscosity of a liquid at known temperatures which comprises:
    (a) introducing the liquid into a vessel;
    (b) positioning said liquid containing vessel within a heat transfer means wherein said heat transfer means is an axially split metallic block;
    (c) rapidly adjusting the temperature of the said liquid by clamping said vessel within said heat transfer means tightly enough to slightly deform the walls of the vessel so that they substantially conform to the internal walls of said heat transfer means;
    (d) stirring said liquid by rotating a stirring means within said liquid at a measured speed;
    (e) simultaneously measuring the power consumed by rotating said stirring means at said speed and the temperature of the heat transfer means; and
    (f) converting the measured power consumption to a viscosity measure and recording the said viscosity measure at the measured temperature.

2. A method as claimed in claim 1 wherein said temperature adjustment and said stirring are commenced substantially simultaneously.

3. A method as claimed in claim 1 wherein the period of time between the commencement of said temperature adjustment of said liquid and the measurement of power consumption is measured.

4. A method as claimed in claim 1 wherein the power consumption is converted by an analog to digital converter and further converted by an empirically generated table held in an electronic memory to yield a test result.

5. An apparatus for measuring the viscosity of a liquid, the apparatus comprising:
    (a) a removable vessel adapted to be filled with a liquid at a location remote from the rest of the apparatus;
    (b) a heat transfer means adapted to accommodate said removable vessel and to rapidly adjust the temperature of its contents wherein said heat transfer means is an axially split metallic block which is adapted to clamp tightly enough around the said vessel to slightly deform its walls so that they conform to the internal walls of said heat transfer means;
    (c) a stirring means adapted to be positioned within said vessel;
    (d) a motor suitable to drive said stirring means;
    (e) a speed controller for controlling the speed of the stirring means;
    (f) temperature measuring means for measuring the temperature of the heat transfer means at any given time;
    (g) power consumption measurement means for measuring the power consumption of the motor at any given time; and,
    (h) conversion means for converting the measured power consumption at any given time to a viscosity measure.

6. An apparatus as claimed in claim 5 wherein the motor is an electric motor.

7. An apparatus as claimed in claim 5 wherein pressure applying means are provided to supply sufficient force on one or both sections of the heat transfer means to press them into contact with the vessel.

8. An apparatus as claimed in claim 7 wherein said pressure applying means is an electrically driven mechanism which is automatically activated upon the commencement of the rotation of said stirring means.

9. An apparatus as claimed in claim 7 wherein said pressure applying means is a mechanically driven mechanism which is automatically activated upon the commencement of the rotation of said stirring means.

10. An apparatus as claimed in claim 5 wherein the motor is connected to the stirrer by a coupling.

11. An apparatus as claimed in claim 10 wherein the stirrer is provided with pins located at either side of the top of the said stirrer adapted to couple with a fixture on the motor shaft such that operation of the motor causes the stirrer to automaticaly rise so that the pins at the top of the stirrer clear the rim of the vessel.

12. An apparatus as claimed in claim 5 wherein there is also provided a timing device which is adapted to be activated at the commencement of said temperature adjustment.

13. An apparatus as claimed in claim 5 wherein there is also provided an analog to digital converter to convert a power consumption reading to a figure which can be converted to give a test result.

14. An apparatus as claimed in claim 5 wherein the vessel is a thin walled aluminum canister.

* * * * *